(12) United States Patent
Korbling et al.

(10) Patent No.: US 8,057,418 B2
(45) Date of Patent: Nov. 15, 2011

(54) DEVICES AND METHODS FOR EXTRACORPOREAL ABLATION OF CIRCULATING CELLS

(75) Inventors: Martin Korbling, Houston, TX (US); J. Donald Payne, Kingwood, TX (US); Christopher L. Coleman, The Woodlands, TX (US); Jon A. Schwartz, Sugar Land, TX (US)

(73) Assignee: Nanospectra Biosciences, Inc., Houston, TX (US)

( * ) Notice: Subject to any disclaimer, the term of this patent is extended or adjusted under 35 U.S.C. 154(b) by 374 days.

(21) Appl. No.: 12/227,843

(22) PCT Filed: Feb. 29, 2008

(86) PCT No.: PCT/US2008/002691
§ 371 (c)(1),
(2), (4) Date: Nov. 26, 2008

(87) PCT Pub. No.: WO2008/108980
PCT Pub. Date: Sep. 12, 2008

(65) Prior Publication Data
US 2009/0156976 A1 Jun. 18, 2009

Related U.S. Application Data

(60) Provisional application No. 60/904,207, filed on Mar. 1, 2007.

(51) Int. Cl.
*A61M 37/00* (2006.01)
*A61M 36/14* (2006.01)
*A61K 51/00* (2006.01)
*G01N 33/53* (2006.01)

(52) U.S. Cl. .................. 604/5.02; 604/5.04; 427/1.17; 435/7.2; 435/7.23

(58) Field of Classification Search ............... 604/5.01, 604/5.02, 5.04; 424/1.17; 435/7.2, 7.23
See application file for complete search history.

(56) References Cited

U.S. PATENT DOCUMENTS

| | | | |
|---|---|---|---|
| 4,321,919 A | 3/1982 | Edelson | |
| 4,398,906 A | 8/1983 | Edelson | |
| 4,428,744 A | 1/1984 | Edelson | |
| 4,464,166 A | 8/1984 | Edelson | |
| 5,984,887 A | 11/1999 | McLaughlin et al. | |
| 6,344,272 B1 | 2/2002 | Oldenburg et al. | |
| 6,528,057 B1 | 3/2003 | Ambrus et al. | |
| 6,530,944 B2 | 3/2003 | West et al. | |
| 6,685,986 B2 | 2/2004 | Oldenburg et al. | |
| 7,201,749 B2 | 4/2007 | Govari et al. | |
| 2003/0118657 A1 | 6/2003 | West et al. | |
| 2004/0191246 A1 | 9/2004 | Connelly et al. | |
| 2006/0141045 A1 | 6/2006 | Bhatt et al. | |
| 2006/0252087 A1 | 11/2006 | Tang et al. | |

FOREIGN PATENT DOCUMENTS

WO WO 2008/108980 9/2008

OTHER PUBLICATIONS

Wu. F. et al, Extracorporeal Focused Ultrasound Surgurey for Treatment of Human Solid Carcinomas: Early Chinese Clinical Experience, Ultrasound in Medicine & Biology, 2004, Vo130. No. 2, Pates 245-260, See entire document.*
Wu. F. Extracorporeal Focused Ultrasound Surgurey for Treatment of Human Solid Carcinomas: Early Chinese Clinical Experience, Ultrasound in Medicine & Biology, 2004, vol. 30. No. 2, Pates 245-260, See entire document.
Malkin. I.R.S. Miniaturized Ultrasound Arrays for Interstitial Albation and Imaging, Ultrasound Medicine & Biology, 2005, vol. 31 No. 11, pp. 1539-1550, See entire document.
Cristofanilli, M., et al., Circulating Tumor Cells, Disease Progression, and Survival in Metastatic Breast Cancer, N. Engl. J. Med., 2004, 351(8): pp. 781-791.
Cristofanilli, M., et al., Circulating Tumor Cells: A Novel Prognostice Factor for Newly Diagnosed Metastatic Breast Cancer, J. Clin. Oncol., 2005. 23(7): pp. 1420-1430.
International Searching Authority/United States (ISA/US), Patent Cooperation Treaty (PCT) International Search Report/Written Opinion, Oct. 7, 2008, United States Patent and Trademark Office; (ISA/US)(PCT), Alexadria, Virginia.

* cited by examiner

*Primary Examiner* — Melanie Hand
(74) *Attorney, Agent, or Firm* — Jackson Walker L.L.P.

(57) ABSTRACT

Methods and devices are provided for the extracorporeal ablation of target cells circulating in blood of an organism. Exogenous material introduced into the blood preferentially associates with target cells (e.g. cancer cells, bacteria, viruses) in the blood. An extracorporeal continuous flow pathway accesses the patient's blood to apply an external energy source to the blood at an ex vivo ablation device in a portion of the extracorporeal continuous flow pathway. The exogenous material interact with the applied energy so as to result in the damage or death of the target cells. The blood is then returned to the body in a continuous-flow pattern. By applying the energy while the blood is in the ex vivo ablation device, shielding of the target cells by the body is reduced and detrimental effects on the organs and tissues of the body are avoided or mitigated.

51 Claims, 6 Drawing Sheets

200

DEVICES AND METHODS FOR EXTRACORPOREAL ABLATION OF CIRCULATING CELLS

CROSS-REFERENCE TO RELATED APPLICATIONS

This application claims the benefit of and priority to U.S. Provisional Patent Application No. 60/904,207, filed on Mar. 1, 2007, which is titled "A Device for the Extracorporeal Ablation of Circulating Cells," and which is hereby incorporated by reference.

BACKGROUND

The present invention relates to devices and methods for the elimination of target cells circulating in the blood of a human or animal. More particularly, the invention involves the use of a continuous-flow, extracorporeal device that ablates target cells by utilizing exogenous material to selectively apply energy to target cells before returning treated blood to the body in a continuous blood flow process.

The in-vivo ablation of solid tumors growing in the body is known in the art and the adverse health effects of such tumors have long been recognized. The presence, however, of certain undesirable cell subsets or organisms (e.g. cancer cells, bacteria, or viruses) in the blood of a human or animal can also have deleterious effects on the health of such humans and animals. The present forms of treatment for diseases associated with these blood borne cell subsets are generally systemic, requiring the treatment of the entire circulating blood. While this systemic approach may be necessary to treat the underlying disease, treating the entire circulating blood with a systemic approach is generally undesirable because such systemic approaches affect not only the undesirable cell subsets but also normal cells and tissues.

The identification of circulating cell subsets for diagnostic purposes is a routine clinical procedure (flow cytometry, etc.). These techniques, however, rely on small blood samples taken from the patient, which are then analyzed. These identification techniques are focused on the enrichment and/or extraction of these cells for diagnostic identification or characterization of a disease.

For example, it has been found that the presence of circulating tumor cells (CTCs) in the blood of patients newly diagnosed with metastatic breast cancer is highly predictive of progression-free, overall survival, and is associated with significant prognostic information. The quantification of CTCs may be based on an automated cell enrichment and immunocytochemical detection system (e.g., the CellSearch System, Veridex, Warren N.J.). In this system, circulating epithelial cells are isolated by antibody-coated magnetic beads in a magnetic field (ferrofluid particles are coated with anti-EpCAM antibodies, two phycoerythron-conjugated anti-cytokeratin antibodies recognizing cytokeratins 8, 18 and 19 to specifically identify epithelial cells, an antibody against CD45 conjugated with allophycocyanin to rule out hematopoietic cells, a nuclear dye DAPI to fluorescently label the cell nuclei, and a permeabilization buffer to allow cytokeratin antibodies entry into epithelial cells), and identified using a. semi-automated fluorescence microscope. Cell images are counted as positive if the morphologic features and staining pattern are consistent with that of an epithelial cell (cytokeratin$^+$, DAPI$^+$, CD45$^-$). Besides antibody-based techniques, it is known in the art to use nucleic acid-based techniques such as RT-PCR to identify CTCs through their expression of differentiation markers (cytokeratins 19 and 20, MUC-1, EGFR, Her-2/neu) or oncofetal antigens (beta human chorionic gonadotropin [beta-HCG]).

The significance of circulating cancer cells has been evaluated in clinical studies. In a prospective multicenter study using the Veridex system, CTCs were detected in ca. 70% of metastatic breast cancer patients with a highest count of 1,491 CTCs per 7.5 ml blood. (see Riethdorf, S. et al., *Detection of circulating tumor cells in peripheral blood of patients with metastatic breast cancer: a validation study of the CellSearch system*, Clin. Cancer Res., 2007. 13(3): p. 920-8.) 61% of metastatic breast cancer patients had >2 CTCs, 47% >6 CTCs per 7.5 ml blood prior to treatment. (see Cristofanilli, M. et al., *Circulating tumor cells, disease progression, and survival in metastatic breast cancer*, N. Engl. J. Med., 2004. 351(8): p. 781-91.) In a prospective multicenter trial on newly diagnosed patients with metastatic breast cancer, 52% of patients had >5 CTCs at baseline with a worse prognosis than patients with <5 CTCs per 7.5 ml blood. (see Cristofanilli, M. et al., *Circulating tumor cells: a novel prognostic factor for newly diagnosed metastatic breast cancer*, J. Clin. Oncol., 2005. 23(7): p. 1420-30.)

Engraftment of CTCs in organ systems other than the primary tumor location requires CTCs with clonogenic potential, sometimes referred to as cancer "stem cells." These cancer "stem cells" have self-renewal capacity similar to normal hematopoietic stem cells and may be capable of forming tumors in subjects. While such cells have not yet been positively identified in the circulating blood of humans having certain forms of cancer, possibly due to, their rare incidence, such theory is consistent with the understanding that stem cells dividing asymmetrically into stem cells and more differentiated cells forming the bulk of the tumor.

Bacteremia is the presence of bacteria in the blood. The blood is normally a sterile environment, but bacteria can enter the bloodstream as a severe complication of infections, during surgery, or due to catheters and other foreign bodies entering the arteries or veins. Bacteremia can have several consequences. The immune response to the bacteria can cause septic shock, which has a relatively high mortality rate. Bacteria can also use the blood to spread to other parts of the body causing infections away from the original site of infection.

Viruses may also circulate in the blood during certain disease states. For example, the viral load of HIV is indicative of disease progression. The reduction in viral load in the blood is one measure of the efficacy of therapy.

Because these types of target cells in the blood generally are rare events and comprise a small number of the total number of cells circulating in the blood stream, most therapeutic techniques focus on the use of drugs to eliminate, inactivate or destroy these cells in-vivo. In the case of cancer cells, for example, chemotherapy or immunotherapies are common techniques. In the case of bacteremia, antibiotics may be used against circulating bacteria. These approaches, however, are not completely effective due in part to increasingly resistant strains of bacteria. Thus, because of the need to avoid significant damage to other circulating blood components and because of the limited number of undesirable cell subsets within the blood, conventional therapeutic techniques are limited in their ability to combat undesirable cell subsets.

Conventional techniques for ablation of stationary in-vivo targets can include the direct application of ablative energy or the use of exogenous materials to transduce the ablative energy at a target site. These techniques can include radiofrequency ablation, thermal ablation using paramagnetic particles activated by alternating magnetic fields, thermal ablation using colloidal metal, plasmonic, or conducting particles activated by electromagnetic radiation, ultrasound based thermal ablation, direct ablation using visible lasers, focused microwave ablation, and similar techniques focused on directing such energy to stationary cell subsets in, for example, a tumor.

Some of these conventional approaches utilized targeting molecules to direct exogenous particles to particular cells or parts of the body. These molecules can be selected from various constructs (peptides, aptamers, antibodies, antibody fragments, and other ligands) that are selective for cell surface receptors on the target cells or that cause the exogenous particle to be internalized by the target cell. The target cell, or the target for the exogenous material, may be an indirect target for ablation, such as endothelial cells of a tumor blood supply. The ablation of these indirect targets may result in the destruction of the ultimate target, such as the tumor itself.

These ablation techniques have comparable methods of cellular elimination that involve the use of light or energy activated molecules that have lethal effect on adjacent cells or tissues. Examples of these comparable methods include photodynamic therapy using photosynthesizers (chemical compound that can be excited by light of a specific wavelength, generally resulting in oxygen radicals). Molecules used for photodynamic therapy include aminolevulinic acid (ALA) and methylaminolevulinate (MAL), among others.

Significantly, the ablative techniques described above are all in-vivo and require energy to be applied to an area of treatment for a specified time, which can range from several seconds to hours. Additionally, most techniques ablate all material within the field of application (e.g. radio frequency ablation, photodynamic therapy, direct laser ablation), thereby resulting in damage to non-target or healthy cells. The use of exogenous energy transducers in these in-vivo procedures allows more specific ablation of solid tissue and tumors. For example, gold nanoshells, comprised of a silica core surrounded by a gold shell, have been designed to absorb near-infrared laser energy. When delivered intravenously to solid tumors, these particles may be activated with a near-infrared laser to thermally ablate the tumor while in the body. In the same vein, the use of targeting ligands with such, nanoparticles may allow an increased level of selectivity of ablation by directing the particle and the applied energy to specific types of cells or a location within the body. U.S. Pat. Nos. 6,344,272 and 6,685,986 teach the compositions and synthesis of one class of nanoparticles. U.S. Pat. No. 6,530,944, which is hereby incorporated by reference, describes localized in-vivo treatments by localized induction of hyperthermia in a cell or tissue by delivering nanoparticles to said cells or tissues and exposing the nanoparticles to an excitation source under conditions where they emit heat. This treatment is applicable to a stationary solid tumor mass.

Other nanoparticles have been described for the in vivo ablation of solid tumors and tissues. For example, paramagnetic particles, gold nanorods and carbon nanotubes have been described, generally with targeting ligands, for the ablation of solid tumors and tissue. These particles have been delivered intravenously or by direct injection into the tumor. These particles may also be delivered through absorption in tumor-targeting cell subsets such as tumor infiltrating lymphocytes. These techniques are applicable to solid tumors.

These techniques have not generally been useful for the ablation or elimination of cells that circulate in blood. These circulating cells either move through an applied energy field too rapidly to allow therapeutic effect or the energy field may not be applied in a manner that can be applied to such cells. For example, visible and near infrared electromagnetic energy have limited depth of penetration through tissue or vessel walls, limiting depth of penetration into the body or blood. Thus, in-vivo activation techniques suffer from the problem of shielding by the body, preventing direct access to the circulating cell subsets. Forms of energy that have greater penetration depth often have undesirable side effects. For example, alternating magnetic fields can result in eddy effects or activation of paramagnetic particles that have cleared from blood but not yet cleared from the body, resulting in adverse effects on healthy tissue.

For the foregoing reasons, conventional techniques for the in-vivo ablation of stationary target cells have many drawbacks for certain applications.

Other conventional techniques, such as the techniques taught in U.S. Pat. No. 6,685,730 use exogenous materials for the purpose of enhanced tissue repair. Such techniques, however, do not teach selective destruction or damaging of cells.

Various extracorporeal devices have been incorporated in other biological processes and methods. For example, dialysis or membrane separation of blood components is a common medical procedure. These techniques are not designed for the treatment of specific cells in the blood, but rather provide for the removal of proteins and molecules normally removed by properly functioning body organs. Apheresis of proteins has also been described for the treatment of diseases, such as dry macular degeneration. These techniques do not treat cells, much less specific targeted cells, during the process.

U.S. Pat. Nos. 4,321,919, 4,398,906, 4,428,744, and 4,464,166, and 5,984,887 describe extracorporeal photopheresis, wherein blood is removed from the body and treated with ultraviolet light and drugs that become active when exposed to such light. The blood is then returned to the body. This technique is being studied in the treatment of some blood and bone marrow diseases (e.g., cutaneous T-cell lymphoma) and graft-vs-host disease (GVHD). In these techniques, mononuclear blood cells are collected by apheresis, treated ex vivo with psoralen, exposed ex vivo to UV light, and finally retransfused to the patient. These techniques are characterized by a batch process (i.e. not a continuous process), because of the nature of the therapy and the length of treatment required, which can last several hours.

Blood warming devices are known in the art and have been used for a variety of purposes. For example, during transfusions, the blood is heated to avoid adverse effects to the patient receiving the transfusion. Following hypothermia, devices have been investigated to heat blood for reinfusion into the patient to elevate body temperatures.

Similarly, extracorporeally elevating the temperature of blood has also been investigated in the treatment of HIV, Kaposi's Sarcoma, cancer and other disorders. Blood was taken out of the body, heated, and then allowed to cool before being returned into the body. Additionally, investigations of whole body hyperthermia for the treatment of cancer have included extracorporeal heating of blood prior to reinfusion to elevate body temperature.

None of the foregoing techniques, however, are useful for targeting specific undesirable cells in the blood.

Likewise, apheresis and similar techniques are known in the art. For example, U.S. Pat. No. 6,528,057 describes a method for reducing viral load by removal of viruses or fragments or components thereof from the blood by extracorporeally circulating blood through hollow fibers which have in the porous exterior surface, immobilized affinity molecules having specificity for viral components. Passage of the fluid through the hollow fibers causes the viral particles to bind to the affinity molecules so as to reduce the viral load in the effluent.

U.S. Pat. No. 5,104,373 describes a method for extracorporeally treating blood samples by one or all of several modalities, including (i) the hyperthermic treating of blood at a reduced pH; (ii) mechanically damaging or lysing blood cells that contain or have been affected by a virus, microorganism or disease state, and so as to render more fragile than other cells; and (iii) subjecting the blood to irradiation. This device, however, is not selective in its application of irradiation to the cells in or components of blood of the patient. Disadvantages of these conventional techniques include failing to preferentially treat the undesirable cell subsets in the irradiated blood stream as opposed to treating the entire irradiated blood stream.

United States Patent Publication No. 2004/0191246 describes a device for the separation of biological cells. The application describes the use of the separated cells for immunotherapy and other means by the in-vivo treatment of bodily fluid, and also makes reference to the "neutralization" of such cells, but does not describe the methods for such neutralization, nor does it describe how such methods distinguish between the target and the remaining blood cells. Additionally, this application contemplates separating the targets from the remaining blood components within the device.

Various devices have been developed for the separation or enrichment of cells from samples of body fluid, yet these devices are not limited to operating on only the sample itself and do not teach treating the entire blood component of a patient. U.S. Patent Publication No. 2006/0252087 describes methods for the separation of cells or target molecules from a body fluid sample. U.S. Patent Publication No. 2006/0141045 describes beads that may be used for cell separation from body fluid samples. U.S. Patent Publication No. 2007/0161051 describes a device with a similar function. Other examples are also described in the literature. These devices, however, are designed to utilize a small fluid sample and therefore are not useful for treating the entire blood volume of a patient.

Accordingly, improved methods are needed that address one or more disadvantages of the prior art.

SUMMARY

The present invention relates to devices and methods for the elimination of target cells circulating in the blood of a human or animal. More particularly, the invention involves the use of a continuous-flow, extracorporeal device that ablates target cells by utilizing exogenous material to selectively apply energy to target cells before returning treated blood to the body in a continuous blood flow process.

In certain embodiments, a method for the extracorporeal ablation of target cells circulating in blood of an organism comprises introducing an exogenous material into the blood wherein the exogenous material is adapted to preferentially associate with the target cells; allowing such exogenous material to preferentially associate with the target cells; providing an extracorporeal continuous flow pathway for accessing the blood and subsequently returning the blood to the body continuously; allowing the blood to flow through the extracorporeal continuous flow pathway; applying an external energy from an external energy source to the blood in a portion of the extracorporeal continuous flow pathway at an ex vivo ablation device; allowing the application of the external energy to activate the exogenous material so as to result in the damage or death of the target cells; and allowing the blood to return continuously to the body from the extracorporeal continuous flow pathway.

The term, "target cells," or "targets" as used herein refers to any undesirable particle, material, or biological agent that is desired to be selectively ablated from the circulating blood of an organism including, but not limited to, any undesirable unicellular or multicellular organism (e.g. cancer cells), certain types of blood cells (e.g., autoreactive T-cells, B-cells), bacteria, virus, fungus, a subset of leukocytes or a monocytes, a parasite, any cell or organism circulating in the blood or an organism, or any combination thereof. It is recognized that although some biological agents such as viruses are not normally encompassed by the plain language meaning of term "cell," for convenience of reference, the term, "target cells," as used herein, is nevertheless intended to not be limited to the typical biological usage of the term "cell."

The term, "exogenous material," as used herein, refers to any material adapted to preferentially associate with the target cells and adapted to activate so as to damage, weaken, or eliminate target cells upon being exposed to external energy from an energy source.

The term "activate," and variations thereof, as used herein, refers to an absorbing, converting, or transduction of energy to heat by exogenous material upon exposure to external energy from an energy source. Alternatively, or additionally, activation of an exogenous material may be by a chemical or physical change of the exogenous material that results in a damaging, weakening, or elimination of the target cells. Suitable examples of exogenous material are provided and discussed further in the disclosure below.

The term "ablation," and variations thereof, as used herein, refers to the elimination, damaging, or weakening of cells by any suitable mechanism including, but not limited to cellular disruption, apoptosis, and/or any other method, which may occur immediately or over time. Ablation may be either by heat or absorbed energy or by metabolic or chemical action triggered by external energy being applied to an exogenous material. Ablation may also include denaturation of proteins; destruction or modification of nucleic acids, cell membranes, or cellular components; the disruption of chemical pathways necessary for cell function, or any other suitable means.

In certain embodiments, a device for the extracorporeal ablation of target cells circulating in blood comprises an extracorporeal continuous flow pathway for accessing the blood and subsequently continuously returning of the blood to the body after treatment; and an energy generator for applying an external energy to the blood in a portion of the extracorporeal continuous flow pathway such that target cells in the blood are preferentially damaged or destroyed.

In certain embodiments, a system for the extracorporeal ablation of targets within blood, said system comprises an extracorporeal continuous flow pathway for access of blood and subsequent continuous return to a biological body; an extracorporeal blood pump for providing a motive force to continuously flow the blood from the biological body and returning the blood to the biological body in a closed loop; an energy source adjacent to said extracorporeal continuous flow pathway; and a plurality of nanoparticles that preferentially associate with target cells within the blood, wherein said nanoparticles are adapted to receive energy from said energy source and release the energy to said target cells.

In certain embodiments, a system for the extracorporeal ablation of targets within blood, said system comprises a continuous-flow, extracorporeal circulation device including an extracorporeal blood flow pathway; an external energy source adjacent a portion of said extracorporeal blood flow pathway; blood containing target cells disposed in said extracorporeal blood flow pathway; and energy absorbing/converting particles attached to said targets.

In certain embodiments, a method for the extracorporeal ablation of target cells circulating in the blood of a biological body comprises attaching, in vivo, energy absorbing/converting particles to circulating blood containing target cells to form conjugates of particles and target cells; extracorporeally circulating the blood outside the biological body; during extracorporeal circulation, exposing the conjugates to external energy while outside the biological body so as to treat the blood; and circulating said treated blood back into the biological body in a continuous flow system.

In certain embodiments, a method for the ablation of target cells circulating in the blood of a biological body comprises extracorporeally circulating blood containing target cells outside a biological body; attaching energy absorbing/converting particles to said target cells in said extracorporeally-circulating blood to form conjugates of particles and target cells; during extracorporeal circulation, exposing the conjugates to external energy while outside the biological body so as to treat the blood; and circulating said treated blood back into the biological body in a continuous flow system.

The features and advantages of the present invention will be apparent to those skilled in the art. While numerous changes may be made by those skilled in the art, such changes are within the spirit of the invention.

BRIEF DESCRIPTION OF THE DRAWINGS

A more complete understanding of the present disclosure and advantages thereof may be acquired by referring to the following description taken in conjunction with the accompanying figures, wherein.

Figure 1A:
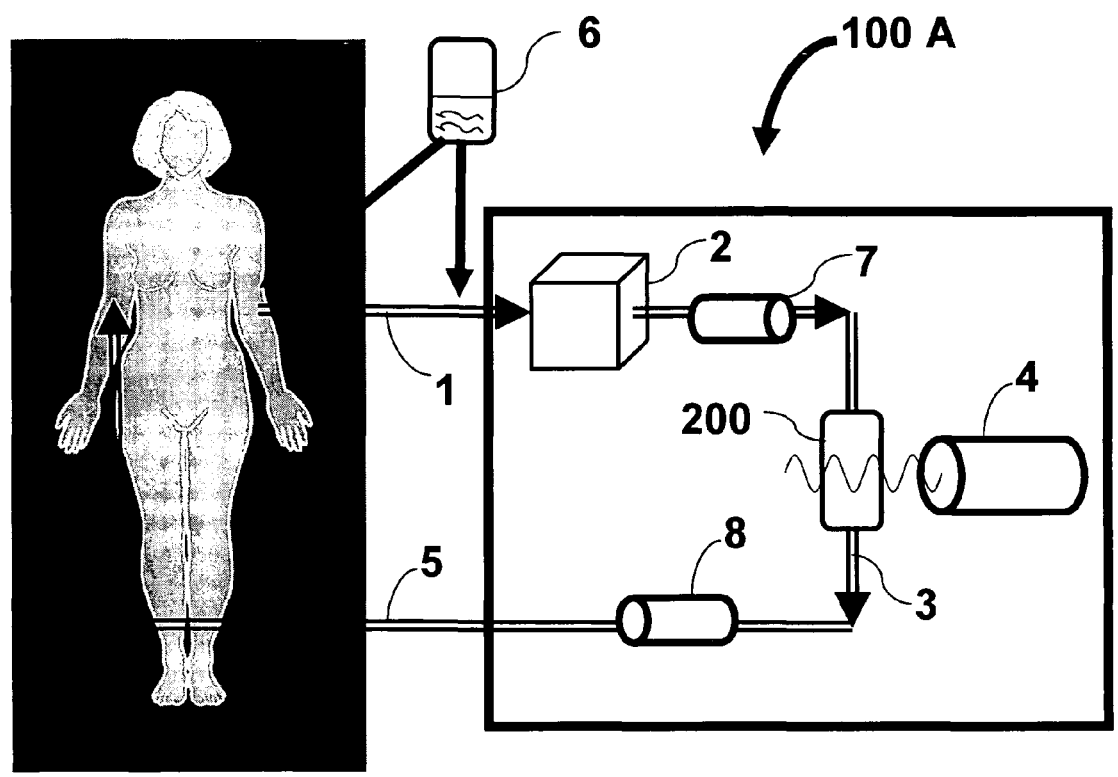
FIG. 1A is a schematic illustration of one embodiment of an extracorporeal device for ablation of target cells in the blood of an organism.

While the present invention is susceptible to various modifications and alternative forms, specific exemplary embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DESCRIPTION OF PREFERRED EMBODIMENTS

The present invention relates to devices and methods for the elimination of target cells circulating in the blood of a human or animal. More particularly, the invention involves the use of a continuous-flow, extracorporeal device that ablates target cells by utilizing exogenous material to selectively apply energy to target cells before returning treated blood to the body in a continuous blood flow process.

The present invention allows for the ablation or weakening of target cells (e.g. cancer cells) circulating in the blood of a human or animal. Exogenous material that preferentially associates with the target cells is introduced into the blood of a patient either in vivo or ex vivo. A continuous flow extracorporeal device may be used to access blood from the body, apply energy to the exogenous material carried by the blood, and then return the blood continuously to the body. As will be explained below in further detail, the energy applied to the blood while passing the ablation device activates the exogenous material so as to result in the ablation of the target cells, while minimizing detrimental effects on other cells, tissues, and organs.

By applying the energy while the blood is in the extracorporeal device, the shielding of the target cells by the body is reduced and detrimental effects on the principal organs and tissues of the body are avoided or mitigated.

Methods to preferentially eliminate these circulating target cells may improve health or clinical outcomes. Depending on the type of target cells to be ablated, the elimination of even some of these target cells may have therapeutic benefits by reducing the probability of adverse clinical outcomes. For example, the reduction of circulating clonogenic tumor cells below an engraftment level significantly reduces the risk of tumor recurrence or metastasis. Likewise, a reduction in the number of circulating cancer cells may reduce or eliminate the number of metastatic events, a reduction in the number of circulating viruses or bacteria may reduce the detrimental effects of the infection.

The use of exogenous material to select target cells directs treatment to the desired target cells with less damage, if any, to normal blood components. By directing treatment to the target cells, a more efficient ablation of target cells may be achieved as compared to conventionally broad therapeutic approaches applied to all of the blood components (such as, for example, chemotherapy).

To facilitate a better understanding of the present invention, the following examples of certain embodiments are given. In no way should the following examples be read to limit, or define, the scope of the invention.

FIG. 1 illustrates a schematic depiction of one embodiment of an extracorporeal device for ablation of target cells in the blood of an organism.

A catheter 1 or similar device is inserted into the vein or artery of a patient and blood is pumped through apparatus 100A and returned to the body through a separate catheter or similar device into the vein or artery 5. The patient's peripheral or central veins/arteries may be accessed by standard procedure, and connected to a tubing set (e.g. equivalent to an apheresis or hemodialysis tubing system). Access and return blood flow may be also achieved through the same double lumen catheter as is routine practice in donor apheresis.

Pump 2 is any device suitable for providing a motive force for continuously flowing blood through apparatus 100A. Various blood pumps suitable for this blood circulation may be used in conjunction with the methods and devices of the present invention. In particular, those pumps used for blood dialysis may be adapted for this purpose. Examples of suitable pumps for use herein include the Gambro Phoenix® or the Fresenius 2008 k. Suitable devices for heating the blood are known in the art.

Blood flow through the extracorporeal continuous flow pathway 1, 3, and 5 may be generated by, for example, roller pumps or the equivalent up to a flow rate of 100 ml/min or higher. In certain embodiments, the blood flow rate ranges from about 60 ml/min to about 100 ml/min, and in other embodiments from about 90 ml/min to about 120 ml/min. The maximum rate may be selected as the rate at which damage to healthy blood cells from this process is minimized.

Optional heater 7 may also allow the heating the blood to maintain a level consistent with its original temperature and/or heating to elevate the temperature of the blood and its components to assist in the ablation of the target cells. In certain embodiments, the function of heater 7 may be integrally incorporated into pump 2.

Prior to or during blood flow through apparatus 100A, exogenous material 6 is infused or otherwise introduced into the blood of the patient. The exogenous material is adapted to preferentially associate with the target cells. Additionally, the exogenous material is adapted to absorb, transduce, or otherwise interact with the energy from energy source 4. Alternatively, the exogenous material may be introduced into the blood during flow through the extracorporeal continuous flow pathway 1, 3, and 5.

While flowing through extracorporeal continuous flow pathway 1, 3, and 5, the continuously flowing blood is exposed to external energy from energy source 4 during flow through a portion of extracorporeal continuous flow pathway 1, 3, and 5. In this case, the blood is exposed to external energy from energy source 4 at ex vivo ablation device 200, which, in this case, forms part of extracorporeal continuous flow pathway 3. When the blood is exposed to energy from energy source 4, the exogenous material absorbs or transduces the energy or is otherwise activated to result in the ablation of the target cells (e.g. by converting the energy to heat). These ablated cells return to the body via continuously flowing pathway 5 and are cleared through normal body clearance mechanisms.

Optional cooler 8 may be any device suitable for cooling the blood, if desired, before returning the blood to the patient via pathway 5. Cooler 8 may function to cool the blood to its original temperature before returning to the body. In certain embodiments, the function of cooler 8 may be integrally incorporated into pump 2. It is further recognized that both heater 7 and cooler 8 may be incorporated into any portion of extracorporeal continuous flow pathway 1, 3, and 5 and further may be in parallel to or in series with any of the elements of apparatus 100A.

Figure 1B:
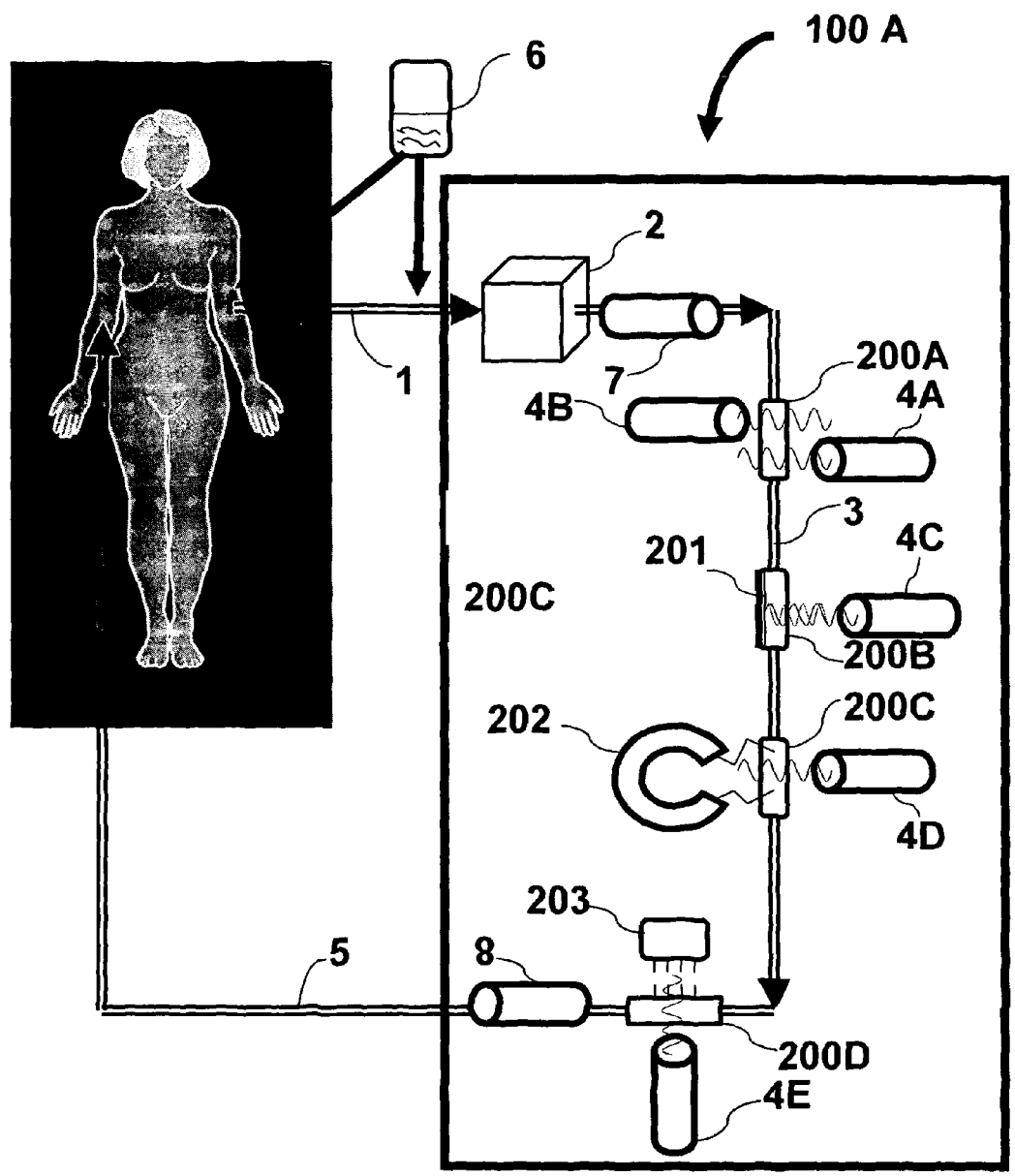
FIG. 1B is a schematic illustration of another embodiment of an extracorporeal device, having additional energy generators and a plurality of ex vivo ablation devices.

FIG. 1B is a schematic illustration of another embodiment of an extracorporeal device, having additional energy generators and a plurality of ex vivo ablation devices.

Apparatus 100B is shown with a plurality of ex vivo ablation devices 200A, 200B, and 200C. Energy sources 4A, 4B, and 4C transmit energy to the blood at ex vivo ablation devices 200A, 200B, and 200C. The use of multiple energy sources 4A, 4B, and 4C allows for a greater concentration of energy to be applied, and in certain embodiments, allows the blood flowing through ex vivo ablation devices 200A, 200B, and 200C to be exposed to more than one type of energy.

Ex vivo ablation device 200A is configured to allow the exposure of external energy to more than one side of ex vivo ablation device 200A. Whether ex vivo ablation device 200A is exposed to energy from more than one side of the device depends on, among other factors, the depth of ex vivo ablation device 200A.

Ex vivo ablation device 200B comprises a reflective backing or surface to allow energy transmitted on one side of the ex vivo ablation device to be reflected back into the ex vivo ablation device so as to further maximize energy exposure to the blood in ex vivo ablation device 200B.

In an alternative embodiment, exogenous material may be gathered in ex vivo ablation device 200C by the use of targeted magnetic particles and/or the application of a magnetic field 202. These magnetic particles may be used in conjunction with other particles, such as nanoshells, or be used for both separation and treatment. Ex vivo ablation device 200C can be designed with a separation chamber to allow the capture of target cells by application of magnetic field 202. Alternatively, magnetic field 202 can hold exogenous material (and consequently, their corresponding or associated target cells) within the chamber for an extended period. In either case, treatment may be applied more directly to and for a longer period of time to the target cells. Magnetic field 202 may be constantly activated or deactivated at desired intervals. Provisions may be made to extract or separate the exogenous material (and consequently, their associated target cells) from ex vivo ablation device 200C.

In an alternative embodiment, an electric current may be applied to a portion of the ex vivo ablation device to provide for the segregation of the target cells into a portion of the ex vivo ablation device. Ex vivo ablation device 200D may include a separation chamber to allow the capture of target cells by application of electric current. In certain embodiments, the electric current may be applied by electrophoresis apparatus 203. Provisions may be made to extract or separate the exogenous material (and consequently, their associated target cells) from ex vivo ablation device 200D.

In certain embodiments, alternative approaches may be used for the capture of the target cells, such as the use of capture molecules (antibodies or fragments thereof, aptamers, peptides, or any other chemical entity that has an affinity for a cell surface molecule on the target cells) within ex vivo ablation device 200C to capture the target cells during circulation for treatment. In this embodiment, the target cells are not required to leave the blood by apheresis or blood draw and are ablated within ex vivo ablation device 200C.

In certain embodiments, ex vivo ablation devices 200A, 200B, and 200C may simply be a portion of tubing or a continuation of extracorporeal continuous flow pathway 1, 3, and 5.

Figure 2:
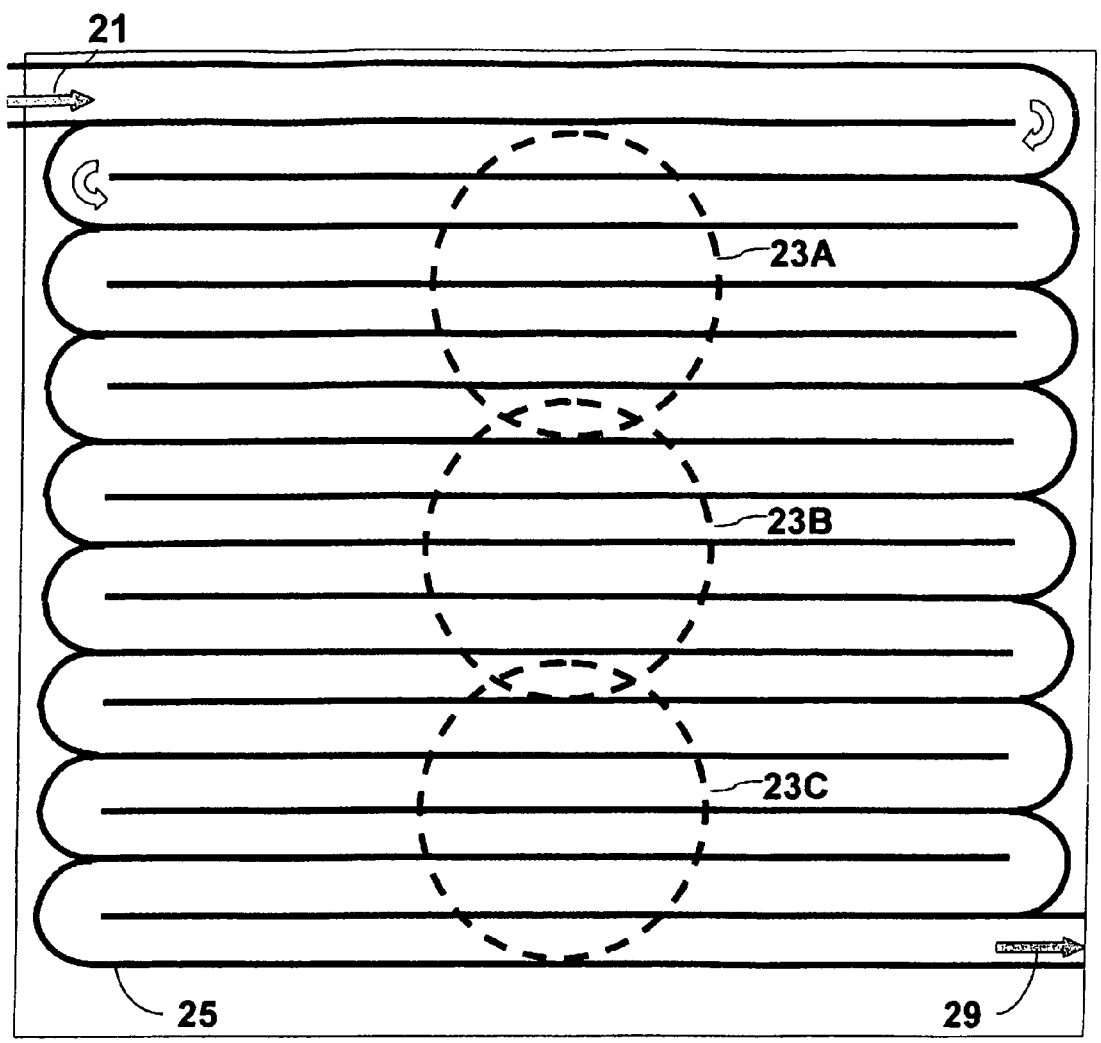
FIG. 2 illustrates an example of one embodiment of an ex vivo ablation device, having channels that allow exposure of the blood to energy during its flow through the device.

FIG. 2 illustrates an example of one embodiment of an ex vivo ablation device, having channels that allow exposure of the blood to energy during its flow through the device.

Blood enters ex vivo ablation device 200 at inlet 21 and exits ex vivo ablation device 200 at outlet 29. In this example, extracorporeal tubing is connected to ex vivo ablation device 200 so as to allow exposure of circulating target cells to an energy source. In this way, the blood continuously flows or circulates through ex vivo ablation device 200 before returning to the body.

Energy may be applied directly to the blood in any portion of ex vivo ablation device 200. In this embodiment, the blood flows through the circuit by way of a series of channels that allow exposure of the blood to the energy source for the desired duration of time. The physical configuration of ex vivo ablation device 200, including the area of exposure, the depth of the device, the number of channels, the diameter of the channels, etc. may be designed to provide the exposure and flow characteristics that optimize the desired energy exposure to the target cells in the blood to the desired effective amount.

By applying the energy while the blood flows through the ex vivo ablation device 200, the shielding of the target cells by the body is reduced and detrimental effects on the principal organs and tissues of the body are avoided or mitigated. In this way, by providing direct access to the blood, the external energy can be focused on the blood and the cells circulating therein, avoiding the application of such energy to the body and damage that may result therefrom. For example, many particles infused or injected into the blood are cleared by the reticuloendothelial system. A broad application of energy to activate these particles may result in the activation of the cleared particles residing in the liver or spleen, resulting in unwanted tissue or organ damage. Thus, by use of this ex vivo ablation device 200, energy may be applied to the blood in a manner that allows more efficient delivery to the target cells to be ablated.

Additionally, in certain embodiments, the material of ex vivo ablation device 200 may designed to be minimally absorptive to the energy applied. For example, if the energy source is near-infrared laser energy, the area circuit where the blood is exposed to the laser may be transmissive or relatively transparent in these wavelengths.

The energy source(s) applied may require several minutes of application for the exogenous material therein to be activated to sufficiently ablate the target cells. In order to expose the exogenous material to the required energy, one or more fields 23A, 23B, or 23C of ex vivo ablation device 200 may be exposed to the energy source. Although, three exposure fields are depicted here, any number of exposure fields may be used in conjunction with the devices and methods of the present invention. If more than one field is exposed, the exposures may be simultaneous in the several fields or determined in a manner to provide for the complete exposure of the blood to the energy source. In certain embodiments, the exposure to the one or more fields 23A, 23B, or 23C is sequential or periodic.

The exposure time of the target cells to the energy source depends on the length of the coiled pathway inside ex vivo ablation device 200, the blood flow rate, and the total blood volume processed. The number of cells exposed to the energy source at any given time depends on, among other factors, the total blood volume inside the device and the area of the exposure fields. In certain embodiments, the ex vivo ablation device exposes circulating target cells to ablating energy multiple times based on the number of total blood volumes pumped through the device.

In one embodiment, the distance between the plates of the device is about 100 μm or greater, allowing a blood flow rate of up to about 100 ml/min. The distance between plates may be kept small to allow a homogenous distribution of cells while passing through ex vivo ablation device 200, and this configuration is governed by, among other factors, the selection of the energy source. In certain embodiments, ex vivo ablation device 200 is configured in a monolayer configuration such that the blood substantially flows through ex vivo ablation device 200 with no more than one layer of cells passing through the exposure area or field of ex vivo ablation device 200 at one time (e.g. no cells overlap one another or "stack up" as they pass through the exposure area of ex vivo ablation device 200).

In one embodiment, the pathway through ex vivo ablation device 200, the energy source, and energy exposure fields 23A, 23B, and 23C are selected to allow exposure of the patient's total blood volume at least once during circulation. The possible exposure times in the device is a function of, among other factors, permissible blood flow rates, the volume held by ex vivo ablation device 200 within the energy illumination field, and the number of passes through the ex vivo ablation device 200. One example of flow rates and device parameters selected for an exposure time of 3.5 minutes is as follows:

Extracorporeal circulation parameters:
Coil tubing length inside the device: 3 meters
Tubing volume inside the device: 70 ml
Blood flow rate: 60 m/min
Total blood volume processed: 3 times $$\frac{\text{Total blood volume coiled tubing [ml]} \times 3}{\text{Blood flow rate [ml/min]}} = \frac{70 \text{ ml} \times 3}{60 \text{ ml/min}} = 3.5 \text{ min}$$

The dimensions of the extracorporeal circuit and the materials of construction will be dependent on the energy source and the required period and intensity of energy illumination. There are a number of commercially available materials and devices that may be adapted for this circuit. For example, see the Therakos Photophoresis System chamber, Exton, Pa., which may be adapted for this purpose.

One of ordinary skill in the art, with the benefit of this disclosure, will appreciate that any of a number and types of energy sources and any of a number and type of exogenous materials, may be selected for use with this device. The energy applied functions in a manner determined by the nature of the energy source and the exogenous material selected.

Figures 3A, 3B:
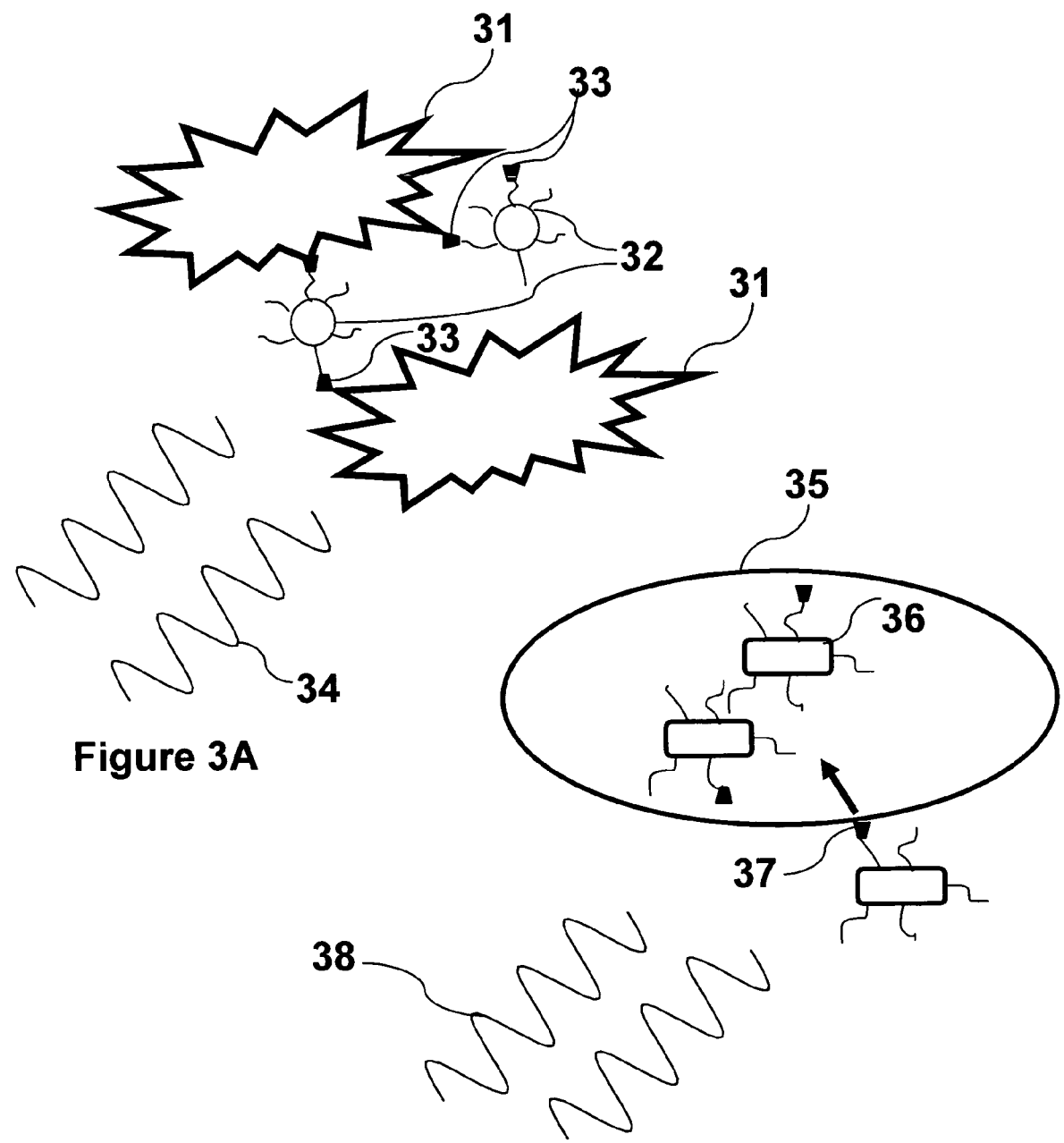
FIG. 3 illustrates the preferential association of exogenous material with the target cells.

FIG. 3 illustrates the method of preferential association of the exogenous material with target cells 31.

The term, "exogenous material," as used herein, refers to any material adapted to preferentially associate with the target cells and adapted to activate so as to damage, weaken, or eliminate target cells upon being exposed to external energy from an energy source. In certain embodiments, the exogenous material is energy-absorbing nanoparticles or microparticles. In another embodiment, the particle may be a magnetic or paramagnetic (e.g., iron oxide particle) particularly when the energy source is an alternating magnetic field. In another embodiment, the particle may be a conducting material (e.g., gold or other metal colloids, nanoshells, nanorods, buckeyballs and carbon nanotubes), particularly when the energy source is radiowaves. Carbon fullerenes, nanocubes, nanostars, and indocyanine green encapsulated in nanoparticles may also be used as suitable exogenous material.

To serve as a transducer, any exogenous material which absorbs strongly in the near-infrared region of the spectrum could also be used. Examples of these materials and their methods of production and functionalization are known in the art. See e.g., U.S. Pat. Nos. 6,344,272 and 6,685,986. These near-infrared transducing materials include, among others: nanoshells (including gold-shell silica core nanoshells, gold-gold sulfide nanoshells and other variants), metal nanorods, nanostars, hollow nanoparticles, nanocages, elliptical "nanorice," carbon particles, buckeyballs, and carbon nanotubes. The absorbed or transduced energy may generate heat to ablate the target cells. In certain embodiments, the exogenous material is a light-activated prodrug.

In certain embodiments, near-infrared absorbing nanoparticles such as nanorods or nanoshells may be conjugated with an antibody to an epithelial cell surface molecule, such as an anti-EGFr antibody. These particles may be inserted into the blood, allowed to bind selectively to circulating cancer cells which have such molecules present on their cell surface. As before, the blood of the patient may then be pumped through an ex vivo ablation device, during which a near-infrared light source is applied. The nanoparticles absorb such energy and generate heat, ablating the associated target cells.

As shown in FIG. 3, exogenous material 32 may be an energy transducing particle (such as a nanoshell or a paramagnetic particle), which has been coated with polyethylene glycol to allow greater circulation time in the blood. Ligand 33 for a molecule on the cell surface of target cell 35 may be affixed to exogenous material 32 or to a coating affixed to exogenous material 32. When exogenous material 32 is infused or otherwise introduced into the blood, exogenous material 32 preferentially binds to the molecule on the surface of target cells 31. The application of external energy 34, such as electromagnetic radiation or an alternating magnetic field, activates exogenous material 32, resulting in the generation of heat to thermally ablate target cells 31.

Examples of the conjugation of ligands to exogenous materials are known in the art.

Alternatively, ligand 37 attached to exogenous material 36 may result in endocytosis (such as by phagocytosis or pinocytosis) of the material by target cell 35. Exogenous material 36 may be an energy absorbing or transducing particle (such as a nanorod), which has been coated with polyethylene glycol to allow greater circulation time in the blood. A ligand 37 for a molecule on the cell surface of target cell 35 may be affixed to exogenous material 36 or to a coating affixed to exogenous material 36. When exogenous material 36 is infused or otherwise introduced into the blood, exogenous material 36 preferentially binds to the molecule on the surface of target cell 35, resulting in the endocytosis of exogenous material 36. The application of external energy 38, such as electromagnetic radiation or an alternating magnetic field, activates exogenous material 36, resulting in the generation of heat to thermally ablate target cell 35.

The properties of exogenous material 36 may also result in the preferential association and endocytosis by the target cells. Photodynamic therapy or photosynthesizer molecules may preferentially associate with lipid receptors on cells, resulting in their uptake by the cell. Upon activation by electromagnetic energy, these molecules may release radicals that result in destruction of the target cells. These materials may also be used with ligands or encapsulated in other materials for preferential association with target cells. The selection of these various exogenous materials and their use is described further herein.

A variety of ligands may be selected for use to preferentially associate the exogenous material with the target cells. The attachment of these ligands to exogenous materials has been extensively described in the scientific literature. The choice of ligand is dependent on the target cells. For example, if the target is a circulating tumor cell of epithelial origin, an antibody or antibody fragment to cytokeratin 8, EpCam or other surface molecules may be used. Alternatively, the ligand may be selected for affinity to the HER2 receptor, the EGF receptor, an integrin, a hormonal receptor, or a variety of other surface molecules. If the target is a circulating bacterium, an antibody or antibody fragment to a surface molecules such as polysaccharides may be used. If the target is a virus such as HIV, an antibody or antibody fragment to GP 120 or 160 may be used. One of ordinary skill in the art, with the benefit of this disclosure, will appreciate, that the ligand may be selected from a variety of proteins, peptides, antibodies, antibody fragments, aptamers or other compounds that has a preferential affinity for the target over other circulating blood components. The ligand selected need not be specific for only the target; the association of the exogenous material with other cells in the body does not affect the ablation of the target cells, because these target cells in the body are not exposed to external energy from the energy source.

In certain embodiments, devices and methods of the present invention allow for the simultaneous or contemporary use of more than one form of energy and more than one form of exogenous material. In addition, the present invention may utilize other energy forms in addition to the described methods. For example, the blood may be heated to a temperature that is non-ablative to healthy blood components prior to the exposure to the energy source. This "background" heating may assist in the subsequent ablation of the target cells. Alternatively, the blood may be cooled by a cooler or in the extracorporeal device to reduce bystander damage from the ablation of the target (e.g. by allowing higher energy application without heating the surrounding blood to a level that damages normal blood cells). Additionally, other therapies or treatments may be contemporaneously applied. Further, the blood may be exposed to ionizing radiation while in the device to create additional damage to the target cells.

The time-at-temperatures relationship necessary to produce thermal ablation leading to cell death has been derived experimentally for a variety of living tissues by various researchers leading to similar results. A well-characterized result, developed by Henriques (McKenzie A L, Physics of thermal processes in laser-tissue interaction, 1990, Phys. Med. Biol., 35(9) 1175-1209) uses an Arrhenius model to derive the critical temperature at which protein is completely denatured indicating complete necrosis. The critical temperature may be expressed as:

$$T(K°) = \frac{\Delta E/R}{\ln(At)} = \frac{7.58 \times 10^4}{\ln(3.1 \times 10^{98} t)}. \qquad [Eq.\ 1]$$

where T is the absolute temperature in Kelvins, ΔE is the tissue activation energy, R is the universal gas constant, A is the frequency factor, and t is time. The above equation predicts complete thermal ablation in 1 second at 60° C., in 1 millisecond at 72° C., and in 1 microsecond at 83° C.

The amount and type of energy from the energy source(s) selected is a function of several variables. For example, in the context of electromagnetic radiation, the wavelength or wavelengths chosen may be selected to minimize the absorption by the other components of the blood, such as hemoglobin or water.

This energy may be in the form of heat, electromagnetic radiation or energy, mechanical energy, ionizing radiation, or a combination thereof. In certain embodiments, the energy is ultraviolet radiation, visible light, infrared light, microwave radiation, radiowaves, or any combination thereof.

While such energy may be absorbed by and affect non-target cells or components of the blood, the adverse effect on the target cells may be beneficial to the patient. In certain embodiments, the wavelengths of electromagnetic energy are selected so as to be minimally absorbed or scattered by the component material of the ex vivo ablation device.

Ablation of the target cell subsets may be by particle-focused hyperthermia, mechanical disruption, ionizing radiation, electromagnetic energy activated chemical methods or other means.

Alternatively, ionizing radiation or other forms of radiation may be applied to the blood while in the ex vivo ablation device. While such method of cellular destruction may not be selective for cancer or bacterial cells, the health benefit from elimination of the target cells may offset depletion of other nucleated cells in the blood. Alternatively, the ionizing radiation dose may be selected to allow ablation of the target cells when combined with other methods described herein.

In another embodiment, the particle may have acoustic properties and the energy source may be acoustic energy including, but not limited to, ultrasound waves. In certain embodiments, the acoustic energy may be transduced by the ultrasound waves to generate heat. In this example, any acoustic particle may be used as the exogenous material for this type of transduction.

Figure 4:
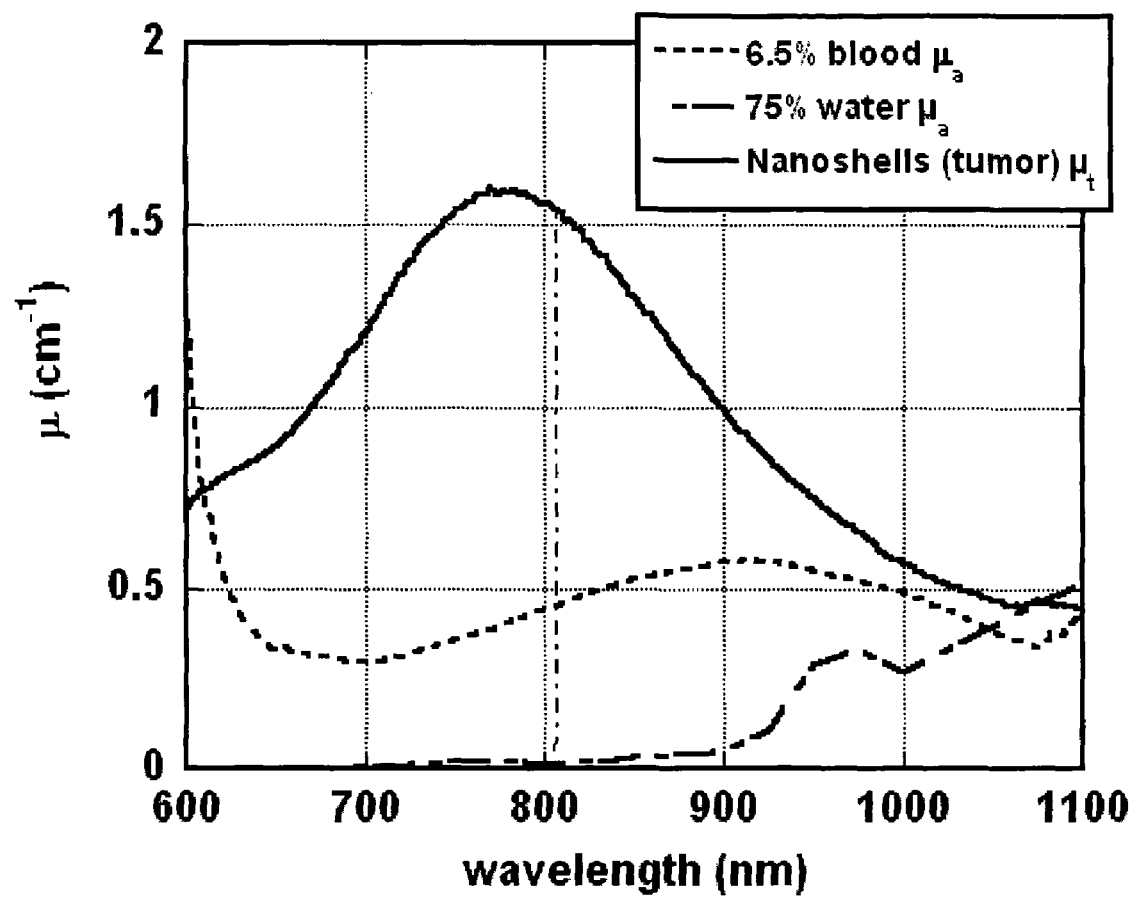
FIG. 4 illustrates the absorbance spectra of the principal optical attenuators in vascular tissue and blood.

FIG. 4 illustrates the extinction spectra of the principal components of human blood, and illustrates the extinction profile of one type of near-infrared transducing exogenous material, a nanoshell. The dashed line marks the wavelength of one laser emission for therapy using near-infrared absorbing particles.

Figure 5A:
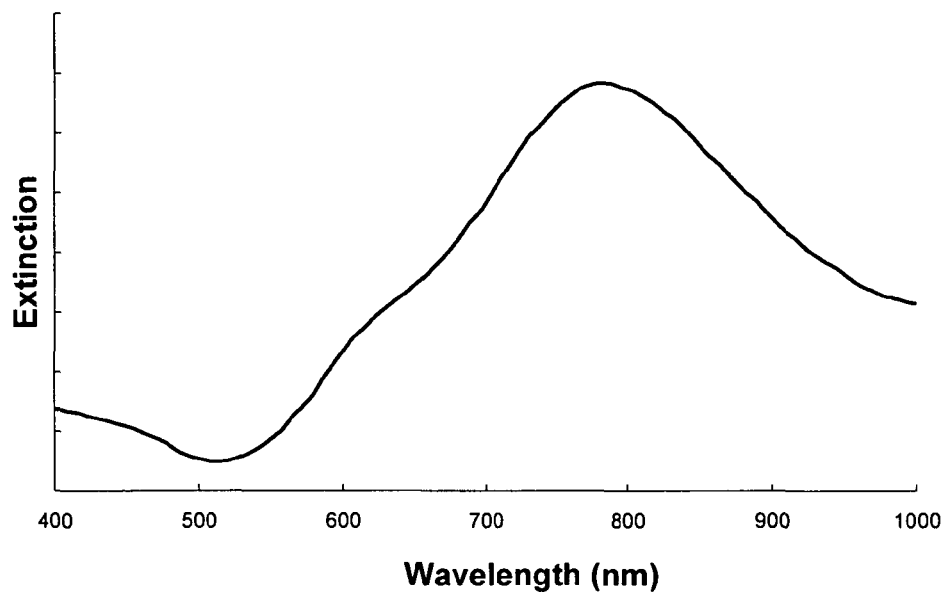
FIG. 5A illustrates the extinction spectra of specific near-infrared absorbing nanoparticles and more specifically depicts the extinction spectra of one size of nanoshell, with a silica core diameter of 120 nm and a gold shell of 14 nm.

FIG. 5A illustrates the extinction spectra of specific near-infrared absorbing nanoparticles and more specifically depicts the extinction spectra of one size of nanoshell, with a silica core diameter of 120 nm and a gold shell of 14 nm.

Figure 5B:
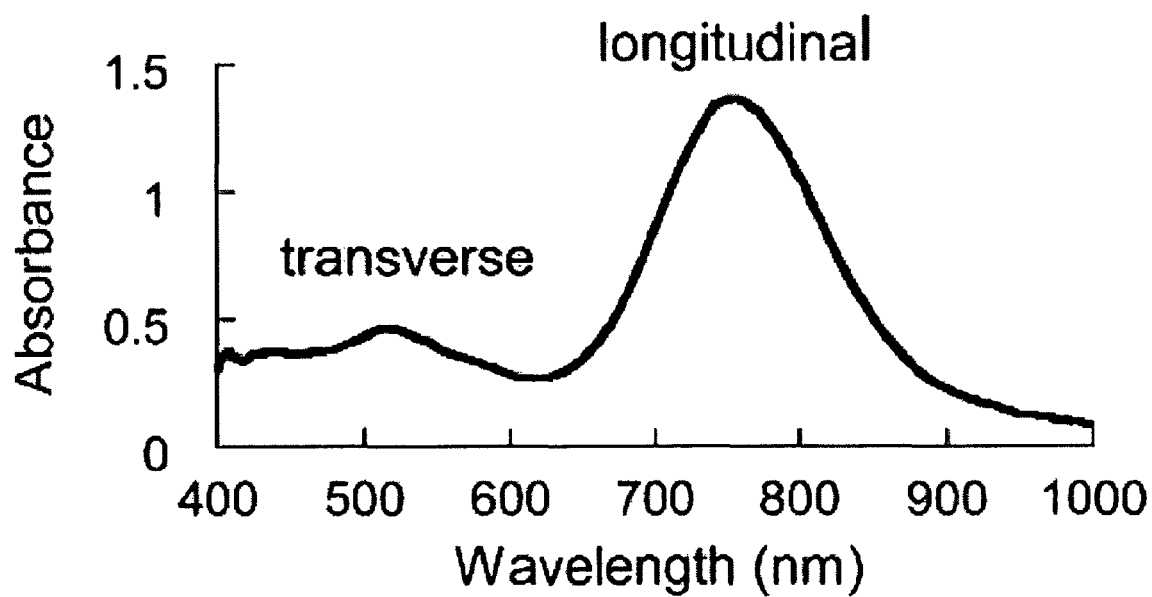
FIG. 5B illustrates the extinction spectra of specific near-infrared absorbing nanoparticles and more specifically depicts the extinction spectra of one size of gold nanorod, with a thickness of 15 nm and a length of 50 nm.

FIG. 5B illustrates the extinction spectra of specific near-infrared absorbing nanoparticles and more specifically depicts the extinction spectra of one size of gold nanorod, with a thickness of 15 nm and a length of 50 nm.

A number of lasers are commercially available in these wavelengths. The laser energy may be applied in a continuous wave or pulsed to provide the optimum exposure of the exogenous material and minimize absorption by other blood components.

In one embodiment, near-infrared radiation may be chosen as the externally applied energy source. In this embodiment, electromagnetic energy, preferably in the spectral region between 650 nm and 1,500 nm, is used as the external energy source. In certain embodiments, the wavelength or wavelengths chosen may be selected to minimize the absorption by the other components of the blood, such as hemoglobin or water.

Alternatively, the energy source may produce radiowaves, or electromagnetic energy in the radio frequencies. In certain embodiments, any exogenous material which is electrically conductive could be utilized to transduce the radio frequency radiation into heat for ablation. There are many examples of exogenous materials that may be used for such transduction, including, among others: iron oxide and other paramagnetic; colloidal metals, including solid gold colloids; carbon nanotubes; nanorods; nanoshells; nanorice; nanostars; and hollow nanoparticles.

Alternatively, the energy source may be an alternating magnetic field. In this embodiment, any exogenous material which has magnetic properties could be utilized to transduce the magnetic field into heat for ablation. There are many examples of exogenous materials that may be used for such transduction, including, among others: iron oxide and other paramagnetic nanoparticles. Various magnetic resonance instruments commercially available may be used as the energy source. However, if this energy source is selected, the composition or location of other components of the extracorporeal device should be compatible with this energy source.

Alternatively, the energy source may activate the exogenous material to ablate the target cells. An example is the use of photosynthesizers to destroy the target cells. Another example is the use of a pro-drug wherein the drug compound is released upon exposure to the energy source.

It is explicitly recognized that any of the elements and features of each of the devices described herein are capable of use with any of the other devices described herein with no limitation. Furthermore, it is explicitly recognized that the steps of the methods herein may be performed in any order except unless explicitly stated otherwise or inherently required otherwise by the particular method.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A method for the extracorporeal ablation of target cells circulating in blood of an organism, said method comprising:
   introducing an exogenous aterial into the blood wherein the exogenous material is adapted to preferentially associate with the target cells;
   allowing such exogenous material to preferentially associate with the target cells;
   providing an extracorporeal continuous flow pathway for accessing the blood and subsequently returning the blood to the body continuously;
   allowing the blood to flow through the extracorporeal continuous flow pathway;
   applying an external energy from an external energy source to the blood in a portion of the extracorporeal continuous flow pathway at an ex vivo ablation device;
   allowing the application of the external energy to activate the exogenous material so as to result in the damage or death of the target cells; and
   allowing the blood to return continuously to the body from the extracorporeal continuous flow pathway.

2. The method of claim 1 wherein the external energy comprises electromagnetic radiation.

3. The method of claim 2 wherein the electromagnetic adiation is ultraviolet radiation, visible light, infrared light, microwave radiation, radiowaves, or any combination thereof.

4. The method of claim 1 wherein the exogenous material is adapted to preferentially absorb electromagnetic radiation.

5. The method of claim 1 wherein the exogenous material is adapted to convert a portion of the electromagnetic radiation to heat upon exposure to electromagnetic radiation.

6. The method of claim 4 wherein the exogenous material is selected from the group consisting of metal colloids, carbon particles, nanoshells, nanorods, buckyballs, carbon fullerenes, nanocubes, nanostars, and indocyanine green encapsulated in nanoparticles.

7. The method of claim 1 wherein the exogenous material comprises photosynthesizers.

8. The method of claim 1 wherein the exogenous material is selected from the group consisting of iron oxides and paramagnetic particles that emit heat when exposed to alternating magnetic fields.

9. The method of claim 1 wherein the exogenous material comprises a light-activated prodrug.

10. The method of claim 1 wherein the external energy comprises acoustic energy.

11. The method of claim 10 wherein the exogenous material is selected from among materials that generate heat when exposed to acoustic energy.

12. The method of claim 1 wherein the preferential association of the exogenous material with the target cells is by way of a ligand attached to the exogenous material.

13. The method of claim 12 wherein said ligand is an antibody, an antibody fragment, an aptamer, a peptide, a chemical entity that has an affinity for a surface molecule on the target cells, or any combination thereof.

14. The method of claim 1 wherein said ligand results in the attachment of the exogenous material to the surface of the target cells.

15. The method of claim 12 wherein said ligand results in the endocytosis of the exogenous material by the target cells.

16. The method of claim 1 wherein the chemical structure of the exogenous material results in the endocytosis of the exogenous material by the target cells.

17. The method of claim 1 wherein the target cells are cancer cells, a type of T-cell or B-cell, a virus, a fungus, a parasite, bacterial cells, or any combination thereof.

18. The method of claim 2 wherein the external energy is a combination of electromagnetic energy and acoustic energy.

19. The method of claim 1 wherein introducing the exogenous material into the blood occurs before allowing the blood to flow through the extracorporeal continuous flow pathway.

20. The method of claim 1 wherein the exogenous material is introduced into the blood during the passage through the extracorporeal continuous flow pathway.

21. The method of claim 1 further comprising elevating the temperature of the blood prior to or during passage through the ex vivo ablation device so as to assist in ablation of the target cells.

22. The method of claim 1 wherein the ex vivo ablation device is made with a reflecting surface to allow energy transmitted on one side of the ex vivo ablation device to be reflected back into the ex vivo ablation device.

23. The method of claim 1 wherein the ex vivo ablation device is exposed to external energy from more than one side of the ex vivo ablation device to provide additional exposure of energy through the blood.

24. The method of claim 1 further comprising providing a cooler and removing energy from the blood by way of the cooler.

25. The method of claim 1 further comprising removing energy from the blood by a cooled or absorptive material.

26. The method of claim 2 further comprising providing a magnetic device and exposing a portion of the extracorporeal continuous flow pathway to a magnetic field so as to segregate the target cells from the blood.

27. The method of claim 26 wherein applying the external energy comprises applying external energy to the segregated target cells.

28. The method of claim 1 wherein a portion of the ex vivo ablation device is adapted to preferentially associate with target cells by way of an antibody or fragment thereof, an aptamer, a peptide, or chemical entity that has an affinity for a cell surface molecule on the target cells so as to capture the target cells circulating in blood; allowing the ex vivo ablation device to capture the target cells; and wherein applying the external energy comprises applying external energy to the captured target cells.

29. The method of claim 1 further comprising applying an external electric field to the ex vivo ablation device to segregate the target cells from the blood.

30. The method of claim 1 wherein the external energy comprises ionizing radiation.

31. The method of claim 1 wherein the external energy from the energy source comprises more than one form of energy.

32. A device for the extracorporeal ablation of target cells circulating in blood comprising:

an extracorporeal continuous flow pathway for accessing the blood and subsequently continuously returning of the blood to the body after treatment; and an energy generator for applying an external energy to the blood in a portion of the extracorporeal continuous flow pathway such that target cells in the blood are preferentially damaged or destroyed.

33. The device of claim 32 further comprising exogenous material for introduction into blood wherein the exogenous material is adapted to preferentially associate with the target cells in the blood.

34. The device of claim 32 wherein the energy generator is adapted to produce acoustic energy.

35. The device of claim 34 wherein the exogenous material comprises a material that generates heat when exposed to acoustic energy.

36. The device of claim 33 wherein the preferential association of the exogenous material with the target cells is by way of a ligand attached to the exogenous material.

37. The device of claim 36 wherein said ligand is an antibody, an antibody fragment, an aptamer, a peptide, a chemical entity that has an affinity /bra surface molecule on the target cells, or a combination thereof.

38. The device of claim 36 wherein said ligand results in the attachment of the exogenous material to the surface of the target cells.

39. The device of claim 36 wherein said ligand results in the endocytosis of the exogenous material by the target cells.

40. The device of claim 33 wherein the chemical structure of the exogenous material results in the endocytosis of the exogenous material by the target cells.

41. The device of claim 33 wherein the target cells are cancer cells, a type of T-cells or B-cells, a virus, a fungus, a parasite or bacterial cells.

42. The device of claim 33 wherein the external energy generator is adapted to produce a combination of electromagnetic energy and acoustic enery.

43. The device of claim 33 wherein the ex vivo ablation device is made with a reflecting surface to allow energy transmitted on one side of the ex vivo ablation device to be reflected back into the ex vivo ablation device.

44. The device of claim 33 wherein the ex vivo ablation device is adapted to receive external energy from more than one side of the ex vivo ablation device to provide additional exposure of energy through the blood.

45. The device of claim 33 further comprising a cooler in the extracorporeal continuous flow pathway for cooling the blood.

46. The device of claim 33 further comprising a magnetic device adapted to expose a portion of the extracorporeal continuous flow pathway to a magnetic field.

47. The device of claim 33 wherein a portion of the ex vivo ablation device comprises an antibody or fragment thereof, an aptamer, a peptide, or other chemical entity that has an affinity for a cell surface molecule on the target cells for capturing the target cells circulating in blood.

48. The device of claim 33 wherein the ex vivo ablation device is adapted to expose an external electric field to the blood to segregate the target cells from the blood.

49. The device of claim 33 wherein the ex vivo ablation device is adapted to expose the blood to ionizing radiation.

50. A system for the extracorporeal ablation of targets within blood, said system comprising:

an extracorporeal continuous flow pathway for access of blood and subsequent continuous return to a biological body;

an extracorporeal blood pump for providing a motive force to continuously flow the blood from the biological body and returning the blood to the biological body in a closed loop;
an energy source adjacent to said extracorporeal continuous flow pathway; and
a plurality of nanoparticles that preferentially associate with target cells within the blood, wherein said nanoparticles are adapted to receive energy from said energy source and release the energy to said target cells.

51. The system of claim 50 wherein said extracorporeal blood pump comprises a blood circuit having an inlet line leading to the extracorporeal blood pump and an outlet line from the extracorporeal blood pump; at least one infusion line comprising at least a pre-infusion branch connected to the inlet line of the blood circuit; and at least one auxiliary fluid container for supplying said at least one infusion line.

* * * * *